United States Patent
Knight et al.

[11] Patent Number: 5,808,244
[45] Date of Patent: Sep. 15, 1998

[54] PROTECTIVE COVER FOR A CONTACT SURFACE FOR A STETHOSCOPE

[76] Inventors: David Knight, P.O. Box 2586, Humble, Tex. 77347; Leslie M. O'Farrell, 1525 Lakeville Dr. #108, Kingwood, Tex. 77339

[21] Appl. No.: 900,140

[22] Filed: Jul. 28, 1997

[51] Int. Cl.⁶ ........................................ A61B 7/02
[52] U.S. Cl. ............................. 181/131; 181/137
[58] Field of Search ...................... 181/131, 137; 381/67

[56] References Cited

U.S. PATENT DOCUMENTS

| | | |
|---|---|---|
| 4,461,368 | 7/1984 | Plourde . |
| 4,867,268 | 9/1989 | Ulert ........................ 181/137 |
| 4,871,046 | 10/1989 | Turner . |
| 5,365,023 | 11/1994 | Lawton . |
| 5,424,495 | 6/1995 | Wurzburger . |
| 5,428,193 | 6/1995 | Mandiberg . |
| 5,448,025 | 9/1995 | Stark et al. . |
| 5,466,898 | 11/1995 | Gilbert et al. . |
| 5,486,659 | 1/1996 | Rosenbush . |
| 5,528,004 | 6/1996 | Wurzburger . |
| 5,564,431 | 10/1996 | Seward . |
| 5,587,561 | 12/1996 | Budayr et al. . |

*Primary Examiner*—Khanh Dang
*Attorney, Agent, or Firm*—Harrison & Egbert

[57] ABSTRACT

A protective cover for a contact surface of a stethoscope having a planar section of film material with a static charge placed therein. The planar section of film material has a top surface and a bottom surface. The section of film material has an area greater than the contact surface of the stethoscope. The top and bottom surfaces are non-adhesive surfaces. The static charge acts on the bottom surface so as to allow the bottom surface to removably cling to the contact surface of the stethoscope. The planar section of film material is applied to a backing surface having an area greater no less than the area of the section of film material.

20 Claims, 2 Drawing Sheets

PROTECTIVE COVER FOR A CONTACT SURFACE FOR A STETHOSCOPE

TECHNICAL FIELD

The present invention relates to devices for preventing contamination of stethoscopes. More particularly, the present invention relates to non-adhesive techniques for applying a protective cover to the contact surface of a stethoscope.

BACKGROUND ART

Acquired infections are an unfortunate fact of hospital stays. It is not uncommon for an infectious organism to spread throughout an entire section of a hospital, particularly within an intensive care unit. Every once in a while, a particularly troublesome organism will affect an entire hospital, and eradication of the organism requires the use of multiple, expensive and toxic antibiotics. Such epidemics cost the hospital, the patient, and insurance companies untold amounts in direct costs, add to the patient's length of stay, and increase morbidity and mortality.

As a result, absolutely every health care worker is encouraged, expected, and required by the hospital as well as the Occupational Safety and Health Administration (OSHA) to wear gloves when they come into contact with patients. Many hospitals now conduct mandatory "universal precautions" courses for all employees that come into contact with patients, prompted by continuing concern with the acquired immune deficiency syndrome virus. These courses, typically repeated on a regular basis, teach that every situation where a patient is to be examined must be considered for the spread of infection. For example, all instruments used to examine patients must either be disposable (such as otoscopicspecula, tongue blades, cotton swabs, and thermometers) or be sterilizable between uses.

It is thus considered unprofessional, irresponsible, and a violation of universal precautions for a health care worker to not wear gloves when examining patients or to neglect to wash hands thoroughly between patients. In such an environment, gloves in various sizes and antiseptic hand cleaners are conspicuously located in cabinets, shelves and racks.

However, the use of certain instruments by hospital personnel must also play a role in hospital-acquired epidemics. Respiratory patients, who are typically at an increased risk of developing pneumonia, usually have foreign objects inserted into their bodies, such as breathing tubes. Respiratory therapists and nurses use stethoscopes every time they visit each and every patient. The stethoscope may become contaminated while examining the lungs of an infected patient, and the therapist then uses the contaminated stethoscope on the next patient. Even if the therapist were to clean the stethoscope and hands, certain microbes known to cause pneumonia are resistant to the most commonly used antibiotics, and contaminants may remain in hard-to-clean crevices. As a result, even the most careful of therapists will unavoidably transfer infections from one patient to the next.

In an emergency room, the situation is similar. All caregivers use a stethoscope, placing it on the chest and back of almost every single patient they encounter. Sometimes the stethoscope is put to the groin or the abdomen to listen for other sounds.

But emergency room patients often have slimy, sweaty skin, and may be unshowered or totally unkempt after being rushed into the hospital. In the worst scenario, trauma room patients arrive in the emergency room covered in blood, HIV-status unknown. As a result, accepted and often mandatory precautions for the arrival of a new patient include donning of goggles, mask, plastic coverall gown, shoe covers, and of course, gloves.

When the patient arrives, the physician always performs the potential life-saving step of applying a stethoscope to listen to the patient's chest immediately, without regard to whatever fluids may be on the chest. The stethoscope is then thrown around the neck, until it is used again on the next patient. The stethoscope is rarely, if ever, cleaned between patients. The bloodied stethoscope may also be stored in the pocket of the physician's white lab coat, where it comes into contact with other items in the pockets. In a large city hospital, this scenario may be repeated many times in a single evening.

In neglecting the role of the stethoscope in the practice of universal precautions, a significant threat to the health and lives of health care workers and patients alike has been permitted to continue. Patients, doctors, hospitals and regulatory agencies have just not adequately considered the stethoscope and the potentially huge health risk it represents.

In the past, various patents have issued relating to devices for preventing the contamination of stethoscopes. Typically, these prior art patents fall in one of three techniques. The first technique is the placement of an envelope around the head of the stethoscope. Another technique is to surround the head of the stethoscope with an elastic sheath. The final technique is the adhesive bonding of a protective cover onto the contact surface of the stethoscope. As will be described hereinafter, these techniques are generally ineffective for preventing contamination of the stethoscope. These devices tend to inhibit the effective use of the stethoscope because of their cumbersome nature.

U.S. Pat. No. 5,466,898 and U.S. Pat. No. 4,871,046 describe "envelope" techniques for preventing contamination from affecting the contact surface of the stethoscope. These envelope devices are folded so as to extend around the surface of the stethoscope. Typically, the envelopes are tied around the back of the stethoscope head so that the envelope is properly secured to the stethoscope. These devices are generally large and expensive. They will require two hands to apply the envelope around the stethoscope.

The elastic sheath technique of preventing contamination is described in U.S. Pat. Nos. 4,461,368, 5,365,023, 5,428,193, 5,486,659, and 5,564,431. In these elastic sheath techniques, a condom-style elastic sheath is placed around the exterior surfaces of the head of the stethoscope. As such, the elastic sheath will effectively prevent contamination from affecting the contact surface of the stethoscope. These elastic sheath forms of stethoscope protection are generally difficult to apply. Normally, it takes two hands to properly apply the elastic sheath around the head of the stethoscope. During the application and removal of such an elastic sheath, direct human contact can occur with the contact surface of the stethoscope. Normally, these elastic sheath forms of contamination prevention are made of latex material. Latex material is non-hypoallergenic. As a result, certain people will suffer allergic reactions when the latex contacts the skin of the person being examined.

The adhesive technique for preventing stethoscope contamination is shown in U.S. Pat. Nos. 5,424,495, 5,448,025, 5,528,004 and 5,587,561. Normally, these techniques provide for the application of a section of plastic to the contact surface of the stethoscope. An adhesive is applied to a bottom surface of the section of plastic material such that the section of plastic material is adhesively secured to the contact surface of the stethoscope. Unfortunately, this adhesive technique will cause a buildup of adhesive residue on the contact surface of the stethoscope. Whenever adhesive residue builds up on the contact surface of the stethoscope, a vector for infection occurs. Normally, physicians are very dissatisfied with such adhesive techniques. These sections of plastic material are often difficult to remove when the physician is wearing latex gloves. Under certain circumstances, two handed manipulation is required so as to properly apply the adhesive sections of material to the contact surface of the stethoscope.

As a result, these prior efforts to prevent contamination of the stethoscope have been ineffective. Typically, physicians will resist the use of such devices because of their complex attachment and removal techniques. As such, there is a strong need to create contamination prevention which is easy to apply, easy to remove, and is non-adhesive.

It is an object of the present invention to provide a protective cover for a stethoscope which is easy to apply and easy to remove.

It is another object of the present invention to provide a protective cover for a stethoscope which does not use adhesives.

It is a further object of the present invention to provide a protective cover for a stethoscope which effectively prevents contamination from affecting the stethoscope.

It is another object of the present invention to provide a protective cover for a stethoscope which is easy to manufacture and relatively inexpensive.

These and other objects and advantages of the present invention will become apparent from a reading of the attached specification and appended claims.

SUMMARY OF THE INVENTION

The present invention is a protective cover for the contact surface of a stethoscope which comprises a planar section of film material having a static charge therein. The planar section of film material has a top surface and a bottom surface. This section of film material has an area greater than the contact surface of the stethoscope. Each of the top surface and the bottom surface are non-adhesive surfaces. The static charge acts on the bottom surface so as to allow the bottom surface to removably cling to the contact surface of the stethoscope. This planar section of film material will typically have a thickness of between 2 and 6 mils. The present invention contemplates the use of a backing surface which is applied to the bottom surface of the planar section of film material. This backing surface typically has an area equal to or greater than the area of the section of film material. Typically, the backing surface will be a flat sheet of material. The backing surface is simply used for the dispensing of the planar section of film material. The planar section of film material is generally centered on the backing surface.

The section of film material is of a generally square configuration. This section of film material can have a circular pattern formed on the top surface. The circular pattern will have an area generally equal to the area of the contact surface. The section of film material has a width generally equal to or greater than a diameter of the contact surface of the stethoscope.

The planar sections of film material and the backing surfaces can be arranged in a stacked configuration within a container or in a roll. Each of the planar sections of film material is sandwiched between adjacent backing surfaces. The container has an opening so that the contact surface of the stethoscope can easily be moved so as to contact the statically charged bottom surface of the planar section of film material after removal of the backing.

The present invention is also a method of operating a stethoscope which comprises the steps of: (1) forming a planar section of film material having a static charge on a surface thereof; and (2) moving the contact surface of the stethoscope into close proximity to the bottom surface of the planar section of film material such that the bottom surface statically clings to the contact surface of the stethoscope. The contact surface of the stethoscope is centered in the circular pattern on the surface of the planar section of film material. The planar section of film material will have corners which extend outwardly of the contact surface of the stethoscope. The stethoscope can be moved onto the human body so that the planar section of film material is interposed between the human body and the contact surface. The planar section of film material is removed from the contact surface of the stethoscope by pulling on a corner of the planar section of film material which extends outwardly of the contact surface so as to release the static adherence of the planar section of film material with the contact surface.

DETAILED DESCRIPTION OF THE INVENTION

Figure 1:
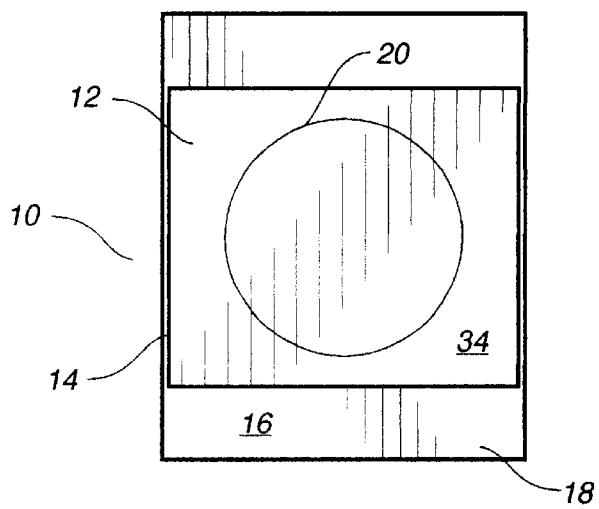
FIG. 1 is a plan view of the present invention showing the planar section of film material as applied to the bottom surface of the backing surface.

FIG. 1 shows the apparatus 10 of the present invention. In particular, in FIG. 1, it can be seen that the apparatus 10 includes a planar section of film material 12 which has a static charge on a bottom surface 14 thereof. The planar section of film material 12 has a rectangular configuration. The planar section of film material is positioned on a top surface 16 of a backing surface 18. A circular pattern 20 is formed on the top surface of the planar section of film material 12. The circular pattern 20 designates the desired placement location of the contact surface of a stethoscope.

In the present invention, the planar section of film material 12 is a generally rectangular or square section of vinyl material. The material which is typically used for the planar section 10 is commonly known as "static cling" vinyl. This "static cling" vinyl has a DC charge embedded on a surface thereof. As such, the bottom surface 14 will cling, by static charge, to another generally flat surface. The planar section of film material will typically have a thickness of between 2 and 6 mils.

The backing surface 18 serves to receive the planar section of film material 12 on the top surface 16 thereof. It can be seen that the planar section of film material 12 is generally centered on the bottom surface 16. The backing surface 18 is typically a very thin and flat sheet of wax paper. The backing surface 18 serves to separate one of the planar section of film material 12 from an underlying of film material. As such, the backing surface 18 facilitates the ability to properly stack the planar section of film material 12.

Figure 2:
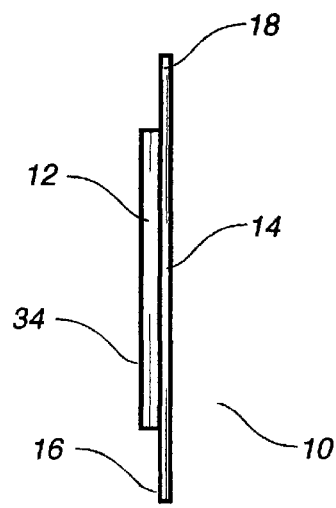
FIG. 2 is a side elevational view of the apparatus of FIG. 1.

FIG. 2 is a side view showing the arrangement of the apparatus. It can be seen that the planar section of film material 12 is generally centered on the top surface 16 of the backing surface 18.

Figure 3:
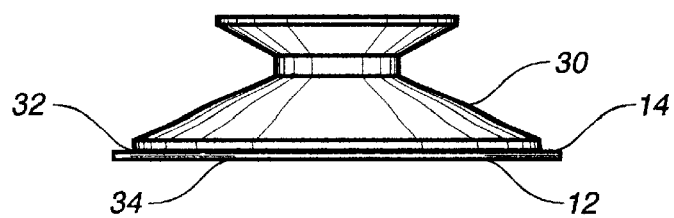
FIG. 3 is a side elevational view showing the planar section of film material as applied to the contact surface of a stethoscope.

FIG. 3 shows the application of a stethoscope 30 onto the planar section of film material 12. As can be seen, the stethoscope 30 has a contact surface 32. In normal use, the contact surface 32 would be the surface of the stethoscope 30 which moves along the human body. So as to avoid contamination of this contact surface 32, the planar section of film material 12 is applied so as to extend over the entire contact surface 32. The planar section of film material 12 is secured to the contact surface 32 by static cling. Since the contact surface 32 is a generally flat surface, the surface 14 of the bottom surface 14 of the planar section of film material 12 will removably cling to the contact surface 32. It is important to note that the planar section of film material 12 has a non-adhesive bottom surface 14 and a non-adhesive top surface. As such, there cannot be any buildup of adhesive material on the contact surface 32 of the stethoscope 30. The thickness of the planar section of film material 12 is such as to avoid any adverse effects to the ability of the physician to hear through the stethoscope. As can be seen in FIG. 3, the planar section of film material 12 has a width generally equal to or greater than the diameter of the contact surface 32 of stethoscope 30. In normal use, the contact surface 32 of the stethoscope 30 will be centered relative to the circular pattern 20 on the top surface 34.

Figure 4:
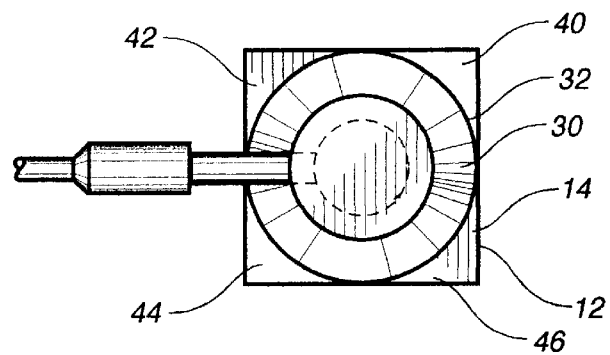
FIG. 4 is a plan view showing the planar section of film material as applied to the contact surface of the stethoscope.

FIG. 4 shows how the stethoscope 30 is placed on the planar section of film material 12. As can be seen in FIG. 4, the planar section of film material 12 has a generally square configuration. The contact surface 32 of the stethoscope 30 has a diameter which generally equals the width of the planar section of film material 12. In this arrangement, the planar section of film material 12 will have corners 40, 42, 44 and 46 extending outwardly from the periphery of the contact surface 32 of the stethoscope 30. These corners 40, 42, 44 and 46 provide an easy-to-reach location for the removal of the planar section of film material 12 from the contact surface 32 of the stethoscope 30. All that is necessary is that the physician grab one of the corners 40, 42, 44 and 46, pull downwardly, and release the planar section of film material 12 from the contact surface 32. This will serve to release the static adherence of the planar section of film material 12 from the contact surface 32.

Figure 5:
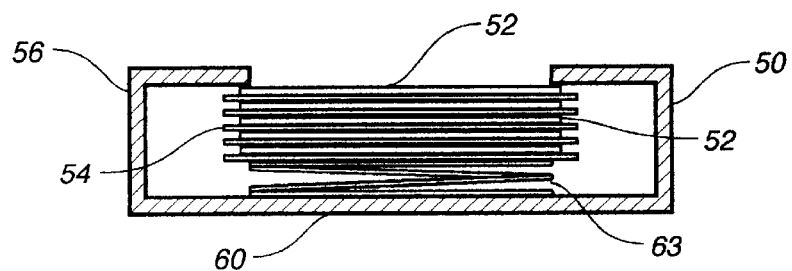
FIG. 5 is a cross-sectional view showing the stacked configuration of the apparatus of the present invention within a container.

FIG. 5 shows a technique for dispensing the planar section of film material. As can be seen in FIG. 5, a container 50 receives a plurality of planar sections of film material 52 and receives a plurality of backing surfaces 54. The planar sections of film material 52 are arranges so that the backing surfaces 54 are interposed between consecutive sections 52. Similarly, the sections 52 are interposed between adjacent backing surfaces 54. The backing surfaces 54 serve to separate adjacent planar sections of film material 52.

In FIG. 5, it can be seen that the container 50 is a box having a top surface 56. An opening 58 is formed in the top surface 56 of the container 50. The opening 58 will have a size such that the planar sections of film material 52 will be generally centered in the opening. The edges of the opening 58 will be disposed adjacent to the outer periphery of the planar sections of film material 52. In one embodiment of the invention, diagonally opposite corners 59 and 61 extend at an angle so as to overlie the corners of the film material 52.

The bottom 60 of the container 50 serves to support the stacked arrangement of backing surfaces 54 and planar sections of film material 52. It can be seen that the top surface 56 slightly overlaps the outer edges of the backing surfaces 54 so as to effectively prevent the backing surfaces 54 from being inadvertently pulled from the container 50 when the planar sections of film material 52 are applied to the contact surface 32 of the stethoscope 30. A mechanism, such as a spring or resilient member 63, can be placed in the container 50 so as to urge the film material toward the opening 58.

Figure 6:
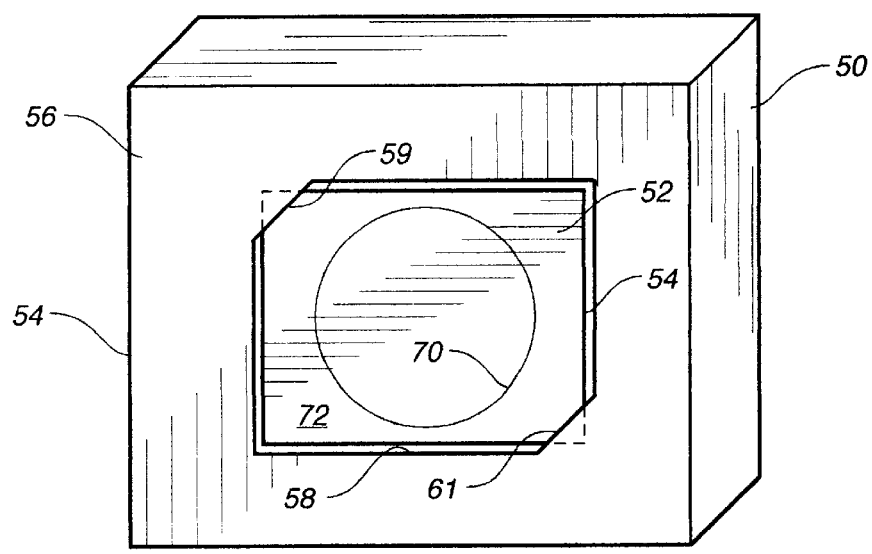
FIG. 6 is a perspective view showing the apparatus of the present invention as contained within the container in a position suitable for dispensing.

FIG. 6 shows how the container 50 can be used for the dispensing of the planar sections of film material 52 for application onto the contact surface 32 of stethoscopes. It can be seen that the circular pattern 70 is formed on the planar section of film material 52. This circular pattern 70 will be visible through transparent or translucent vinyl which forms the planar section of film material. The planar section of film material 52 is generally centered on the backing surface 54. The planar section of film material 52 is centered within the opening 58 of the container 50. The edges of the opening 58 on the top surface 56 of the container 50 overlap the outer peripheral edges of the backing surface 54.

In normal use, the contact surface of the stethoscope 30 is moved so as to be in proximity with the bottom surface 72 of the planar section of film material 52. When the contact surface 32 of the stethoscope 30 is brought into close proximity with the bottom surface 72, the bottom surface 72 with the planar section of film material 52 will statically cling to the contact surface 32. The stethoscope 30 can then be moved away from the top surface 56 of the container 50 so as to cause the planar section of film material 52 to be removed from the container. All that is necessary is for the physician to grasp the exterior surface of the container 50 and to move the stethoscope 30 toward the circular pattern 70 on the planar section of film material 52. No complex manipulations are required of the stethoscope 30 or the container 50. There is no risk of contamination between the hands of the physician and the contact surface 32 of the stethoscope 30. After an examination of a patient has occurred, the physician can simply grab one of the corners of the planar section of film material 52 so as to release the "static cling" and to remove the planar section of film material 52 from the contact surface 32 of the stethoscope 30.

For the application of another planar section of film material, it is only necessary to remove the backing surface 54 so as to expose the next planar section of film material in the stacked configuration within the container 50.

As can be seen the present invention achieves a number of advantages over the prior art. First, and foremost, contamination of the contact surface 32 of the stethoscope 30 is effectively prevented. The planar section of film material serves as a barrier between the body of the patient and the contact surface 32 of the stethoscope 30. As such, contamination with disease and bacteria is effectively prevented from residing on the contact surface 32. Since no adhesives are used in the present invention, there will be no adhesive buildup. The adverse health effects from the application of adhesives is effectively avoided. The present invention will eliminate the need to periodically clean the adhesive buildup from the surface of the stethoscope. The planar section of film material is easily applied and removed without any complex manipulation by the physician. Importantly, since the static charge in the planar section of film material 12 is reduced after the initial application of the planar section of film material 12, it will be very difficult for the physician to inadvertently or intentionally reuse the protective cover of the present invention. Disposal, after use, is encouraged because of the relatively low cost of the protective cover of the present invention.

The foregoing disclosure and description of the invention is illustrative and explanatory thereof. Various changes in the details of the illustrated construction or in the steps of the described method can be made within the scope of the appended claims without departing from the true spirit of the invention. The present invention should only be limited by the following claims and their legal equivalents.

We claim:

1. A protective cover for a contact surface of a stethoscope comprising:

a planar section of film material having a static charge therein, said planar section of film material having a top surface and a bottom surface, said planar section of film material having an area no less than a contact surface of the stethoscope, each of said top surface and said bottom surface being non-adhesive surfaces, said static charge acting on said bottom surface so as to allow said bottom surface to removably cling to the contact surface of the stethoscope.

2. The protective cover of claim 1, further comprising:

a backing surface applied to said top surface, said backing surface having an area greater than said area of said planar section of film material.

3. The protective cover of claim 2, said backing surface being a flat sheet of paper.

4. The protective cover of claim 1, said planar section of film material having a thickness of between 2 and 6 mils.

5. The protective cover of claim 1, said section of film material being of a generally square configuration.

6. The protective cover of claim 5, said planar section of film material having a circular pattern formed thereon, said circular pattern having an area generally equal to the area of the contact surface.

7. The protective cover of claim 6, said planar section of film material having a width generally no less than a diameter of the contact surface.

8. An apparatus for dispensing protective covers for protecting a contact surface of a stethoscope comprising:

a plurality of planar sections of film material having a static charge therein, each of said plurality of planar section of film material having a non-adhesive top surface and a non-adhesive bottom surface, said static charge acting on said bottom surface so as to allow said bottom surface to removably cling to the contact surface of the stethoscope; and a plurality of backing surfaces each having an area no less than an area of each of said plurality of planar sections of film material, each of said plurality of planar sections of film material being sandwiched between adjacent backing surfaces of said plurality of backing surfaces.

9. The apparatus of claim 8, each of said plurality of planar sections of film material having a thickness of between 2 and 6 mils.

10. The apparatus of claim 8, each of said plurality of planar sections of film material being generally centered relative to said plurality of backing surfaces.

11. The apparatus of claim 8, each of said plurality of planar sections of film material being of a generally square configuration.

12. The apparatus of claim 11, each of said plurality of planar sections of film material having a circular pattern formed on said top surface, said circular pattern having an area generally equal to the area of the contact surface.

13. The apparatus of claim 8, further comprising:

a container having said plurality of planar sections of film material and said plurality of backing surfaces received therein in a stacked configuration.

14. The apparatus of claim 13, said container having an opening in a surface thereof, said opening having an area greater than an area of each of said plurality of planar sections of film material, said opening having an extension overlying a portion of each of said plurality of planar sections of film material.

15. A method of operating a stethoscope so as to resist contamination comprising the steps of:

forming a planar section of film material having a static charge placed on a bottom surface thereof, said planar section of film material having an area no less than an area of a contact surface of the stethoscope; and moving said contact surface of the stethoscope into close proximity to said bottom surface of said planar section of film material such that said bottom surface statically clings to the contact surface of the stethoscope.

16. The method of claim 15, said step of forming comprising the step of:

placing a top surface of said planar section of film material onto a backing surface.

17. The method of claim 15, said step of forming comprising the steps of:

forming a circular pattern on said top surface of said planar section of film material; and forming said planar section of film material into a generally rectangular configuration, said circular pattern being generally centered on said planar section of film material.

18. The method of claim 17, said step of moving comprising:

contacting said contact surface and said planar section of film material such that said contact surface is centered in said circular pattern, said planar section of film material having corners extending outwardly of said contact surface.

19. The method of claim 18, further comprising the step of:

moving the stethoscope onto a human body such that said planar section of film material is interposed between the human body and the contact surface of the stethoscope, said planar section of film material having an area greater than an area of said contact surface.

20. The method of claim 19, further comprising the steps of:

removing the stethoscope from contact with the human body; and pulling on a corner of said planar section of film material that extends outwardly of said contact surface so as to release a static adherence of said planar section of film material with said contact surface.

* * * * *